United States Patent
Simon et al.

(10) Patent No.: US 6,761,891 B1
(45) Date of Patent: Jul. 13, 2004

(54) MEDICAMENT FOR TREATING A MANIFESTED LYME DISEASE

(75) Inventors: Markus M. Simon, Freiburg (DE); Weimin Zhong, Freiburg (DE); Reinhard Wallich, Heidelberg (DE); Michael D. Kramer, Pfungstadt (DE)

(73) Assignee: Max-Planck-Gesellschaft zur Förderung der Wissenschaften E.V., München (DE)

( * ) Notice: Subject to any disclaimer, the term of this patent is extended or adjusted under 35 U.S.C. 154(b) by 0 days.

(21) Appl. No.: 09/508,096

(22) PCT Filed: Sep. 15, 1998

(86) PCT No.: PCT/EP98/05852

§ 371 (c)(1),
(2), (4) Date: Jul. 6, 2000

(87) PCT Pub. No.: WO99/14345

PCT Pub. Date: Mar. 25, 1999

(30) Foreign Application Priority Data

Sep. 16, 1997 (DE) .......................................... 197 40 735

(51) Int. Cl.$^7$ ........................ A61K 39/02; A61K 49/00; A61K 39/395; A61K 39/40; A61K 39/38

(52) U.S. Cl. ...................... 424/190.1; 424/9.1; 424/9.2; 424/130.1; 424/139.1; 424/141.1; 424/150.1; 424/164.1; 424/184.1; 424/185.1; 435/7.1; 530/300; 530/350

(58) Field of Search ...................... 424/9.1, 9.2, 130.1, 424/139.1, 141.1, 150.1, 164.1, 184.1, 185.1, 190.1; 435/7.1; 530/300, 350

(56) References Cited

FOREIGN PATENT DOCUMENTS

WO      94 25596      11/1994

OTHER PUBLICATIONS

Bockenstedt, L.K., et al., "Borrelia burgdorferi strain–specific osp C–mediated immunity in mice." Infection and Immunity, vol. 65, No. 11, pp. 4661–4667, Nov., 1997.*

Barthold et al., "Protective and arthritis–resolving activity in sera of mice infected with Borrelia burgdorferi", Clinical Infectious Diseases, vol. 25, No. 1 suppl, Jul. 1997, pp. s9–s17.

Edelman et al, "The seventh international congress on lyme borreliosis: progress on the development of Lyme disease vaccines", Vaccine, vol. 15, No. 5, Apr. 1997, pp. 463–464.

Gilmore et al., "Outer surface protein C (OspC), but not p39, is a protective immunogen against a tick–transmitted Borrelia burgdorferi challenge . . . " Infection and Immunity, vol. 64, No. 6, Jun. 1996, pp. 2234–2239.

Zhong et al., "Therapeutic passive vaccination against chronic Lyme disease in mice", PNAS, vol. 94, No. 23, Nov. 11, 1997, pp. 12533–12538.

* cited by examiner

Primary Examiner—Rodney P Swartz
(74) Attorney, Agent, or Firm—Rothwell, Figg, Ernst & Manbeck, P.C.

(57) ABSTRACT

A pharmaceutical composition for treating Lyme disease contains an antibody as an active agent which is specific for the 24 kDa antigen (OspC) of *B. burgdorferi*, preferably an antibody which is specific for the 24 kDa antigen (OspC) of *B. burgdorferi* having the sequence shown in SEQ ID NO.2.

18 Claims, 4 Drawing Sheets

Figure 3: SEQ ID NO.2
Gene sequence and protein sequence of the outer surface protein C (OspC) isolated from the European Borrelia burgdorferi stricto strain ZS7

```
      atgaaaaagaatacattaagtgcaatattaatgactttattttatttatatcttgtaat
  1   ---------+---------+---------+---------+---------+---------+   60
      tacttttttcttatgtaattcacgttataattactgaaataaaaataaatatagaacatta
      M  K  K  N  T  L  S  A  I  L  M  T  L  F  L  F  I  S  C  N aattcaggaaaagatgggaatgcatctgcaaattctgctgatgagtctgttaaagggcct
 61   ---------+---------+---------+---------+---------+---------+  120
      ttaagtccttttctacccttacgtagacgtttaagacgactactcagacaatttcccgga
      N  S  G  K  D  G  N  A  S  A  N  S  A  D  E  S  V  K  G  P aatcttacagaaataagtaaaaaaattacggattctaatgcggttttacttgctgtgaaa
121   ---------+---------+---------+---------+---------+---------+  180
      ttagaatgtctttattcattttttttaatgcctaagattacgccaaaatgaacgacacttt
      N  L  T  E  I  S  K  K  I  T  D  S  N  A  V  L  L  A  V  K gaggttgaagcgttgctgtcatctatagatgagcttgctaaagctattggtaaaaaaata
181   ---------+---------+---------+---------+---------+---------+  240
      ctccaacttcgcaacgacagtagatatctactcgaacgatttcgataaccattttttat
      E  V  E  A  L  L  S  S  I  D  E  L  A  K  A  I  G  K  K  I aaaaacgatggtagtttagataatgaagcaaatcgcaacgagtcattgttagcaggagct
241   ---------+---------+---------+---------+---------+---------+  300
      ttttgctaccatcaaatctattacttcgtttagcgttgctcagtaacaatcgtcctcga
      K  N  D  G  S  L  D  N  E  A  N  R  N  E  S  L  L  A  G  A tatacaatatcaaccttaataacacaaaaattaagtaaattaaacggatcagaaggttta
301   ---------+---------+---------+---------+---------+---------+  360
      atatgttatagttggaattattgtgttttaattcatttaatttgcctagtcttccaaat
      Y  T  I  S  T  L  I  T  Q  K  L  S  K  L  N  G  S  E  G  L aaggaaaagattgccgcagctaagaaatgctctgaagcatttactgacaaattaaaaaat
361   ---------+---------+---------+---------+---------+---------+  420
      ttccttttctaacggcgtcgattctttacgagacttcgtaaatgactgtttaattttta
      K  E  K  I  A  A  A  K  K  C  S  E  A  F  T  D  K  L  K  N gagcacgcaagtcttggtaaaaaagatgctactgatgatgatgcaaaaaaagctatttta
421   ---------+---------+---------+---------+---------+---------+  480
      ctcgtgcgttcagaaccatttttctacgatgactactactacgttttttcgataaaat
      E  H  A  S  L  G  K  K  D  A  T  D  D  D  A  K  K  A  I  L aaagcaaatgcagcgggtaaagataagggcgttgaagaacttgaaaagttgtccggatca
481   ---------+---------+---------+---------+---------+---------+  540
      tttcgtttacgtcgcccatttctattcccgcaacttcttgaacttttcaacaggcctagt
      K  A  N  A  A  G  K  D  K  G  V  E  E  L  E  K  L  S  G  S ttagaaagcttatcagaagcagctaaagagatgcttgctaattcagttaaagagcttaca
541   ---------+---------+---------+---------+---------+---------+  600
      aatctttcgaatagtcttcgtcgatttctctacgaacgattaagtcaatttctcgaatgt
      L  E  S  L  S  E  A  A  K  E  M  L  A  N  S  V  K  E  L  T agtcctgttgtggcagaaagtccaaaaaaaccttaa
601   ---------+---------+---------+------  636
      tcaggacaacaccgtctttcaggttttttggaatt
      S  P  V  V  A  E  S  P  K  K  P  *
```

Figure 4

| | | |
|---|---|---|
| plasmid name: | pG.OspC-ZS | size: 5,5 kb |
| insert: (species) | OspC gene without signal sequence (B.burgdorferi ZS7) PCR fragment | insert size: 0.6 kb |
| Cloning vector: | pGEX-2T (Pharmacia Biotech) | |
| Cloning site: | BamHI/EcoRI | |
| Antibiotic resistance: | Amp' | |
| Application date: | 1.11.94 | |

```
Thrombin
(Seq ID No:6) Leu Val Pro Arg Gly Ser Asn Asn Ser Lys Lys Pro *
(Seq ID No:5) CTG GTT CCG CGT GGA TCC AAT AAT TCA - OspC - AAA AAA CCT TAG AAT TCA
```

BamHI Eco RI

SEQUENCE LISTING

<160> NUMBER OF SEQ ID NOS: 6

<210> SEQ ID NO 1
<211> LENGTH: 636
<212> TYPE: DNA
<213> ORGANISM: Borrelia burgdorferi
<220> FEATURE:
<221> NAME/KEY: CDS
<222> LOCATION: (1)..(633)
<223> OTHER INFORMATION:

<400> SEQUENCE: 1

```
atg aaa aag aat aca tta agt gca ata tta atg act tta ttt tta ttt      48
Met Lys Lys Asn Thr Leu Ser Ala Ile Leu Met Thr Leu Phe Leu Phe
1               5                   10                  15 ata tct tgt aat aat tca gga aaa gat ggg aat gca tct gca aat tct      96
Ile Ser Cys Asn Asn Ser Gly Lys Asp Gly Asn Ala Ser Ala Asn Ser
                20                  25                  30 gct gat gag tct gtt aaa ggg cct aat ctt aca gaa ata agt aaa aaa     144
Ala Asp Glu Ser Val Lys Gly Pro Asn Leu Thr Glu Ile Ser Lys Lys
            35                  40                  45 att acg gat tct aat gcg gtt tta ctt gct gtg aaa gag gtt gaa gcg     192
Ile Thr Asp Ser Asn Ala Val Leu Leu Ala Val Lys Glu Val Glu Ala
        50                  55                  60 ttg ctg tca tct ata gat gag ctt gct aaa gct att ggt aaa aaa ata     240
Leu Leu Ser Ser Ile Asp Glu Leu Ala Lys Ala Ile Gly Lys Lys Ile
65                  70                  75                  80 aaa aac gat ggt agt tta gat aat gaa gca aat cgc aac gag tca ttg     288
Lys Asn Asp Gly Ser Leu Asp Asn Glu Ala Asn Arg Asn Glu Ser Leu
                85                  90                  95 tta gca gga gct tat aca ata tca acc tta ata aca caa aaa tta agt     336
Leu Ala Gly Ala Tyr Thr Ile Ser Thr Leu Ile Thr Gln Lys Leu Ser
            100                 105                 110 aaa tta aac gga tca gaa ggt tta aag gaa aag att gcc gca gct aag     384
```

-continued

```
Lys Leu Asn Gly Ser Glu Gly Leu Lys Glu Lys Ile Ala Ala Ala Lys
            115                 120                 125 aaa tgc tct gaa gca ttt act gac aaa tta aaa aat gag cac gca agt      432
Lys Cys Ser Glu Ala Phe Thr Asp Lys Leu Lys Asn Glu His Ala Ser
130                 135                 140 ctt ggt aaa aaa gat gct act gat gat gat gca aaa aaa gct att tta      480
Leu Gly Lys Lys Asp Ala Thr Asp Asp Asp Ala Lys Lys Ala Ile Leu
145                 150                 155                 160 aaa gca aat gca gcg ggt aaa gat aag ggc gtt gaa gaa ctt gaa aag      528
Lys Ala Asn Ala Ala Gly Lys Asp Lys Gly Val Glu Glu Leu Glu Lys
                165                 170                 175 ttg tcc gga tca tta gaa agc tta tca aaa gca gct aaa gag atg ctt      576
Leu Ser Gly Ser Leu Glu Ser Leu Ser Lys Ala Ala Lys Glu Met Leu
            180                 185                 190 gct aat tca gtt aaa gag ctt aca agt cct gtt gtg gta gaa agt cca      624
Ala Asn Ser Val Lys Glu Leu Thr Ser Pro Val Val Val Glu Ser Pro
        195                 200                 205 aaa aaa cct taa                                                      636
Lys Lys Pro
210
```

<210> SEQ ID NO 2
<211> LENGTH: 211
<212> TYPE: PRT
<213> ORGANISM: Borrelia burgdorferi

<400> SEQUENCE: 2

```
Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Ala Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Leu Ala Lys Ala Ile Gly Lys Lys Ile
65                  70                  75                  80

Lys Asn Asp Gly Ser Leu Asp Asn Glu Ala Asn Arg Asn Glu Ser Leu
                85                  90                  95

Leu Ala Gly Ala Tyr Thr Ile Ser Thr Leu Ile Thr Gln Lys Leu Ser
            100                 105                 110

Lys Leu Asn Gly Ser Glu Gly Leu Lys Glu Lys Ile Ala Ala Ala Lys
        115                 120                 125

Lys Cys Ser Glu Ala Phe Thr Asp Lys Leu Lys Asn Glu His Ala Ser
130                 135                 140

Leu Gly Lys Lys Asp Ala Thr Asp Asp Asp Ala Lys Lys Ala Ile Leu
145                 150                 155                 160

Lys Ala Asn Ala Ala Gly Lys Asp Lys Gly Val Glu Glu Leu Glu Lys
                165                 170                 175

Leu Ser Gly Ser Leu Glu Ser Leu Ser Lys Ala Ala Lys Glu Met Leu
            180                 185                 190

Ala Asn Ser Val Lys Glu Leu Thr Ser Pro Val Val Val Glu Ser Pro
        195                 200                 205

Lys Lys Pro
210
```

<210> SEQ ID NO 3

-continued

```
<211> LENGTH: 29
<212> TYPE: DNA
<213> ORGANISM: Borrelia burgdorferi

<400> SEQUENCE: 3
atggatccaa taattcagga aaagatggg                                     29

<210> SEQ ID NO 4
<211> LENGTH: 33
<212> TYPE: DNA
<213> ORGANISM: Borrelia burgdorferi

<400> SEQUENCE: 4
atgaattcct aaggtttttt tggactttct acc                                33

<210> SEQ ID NO 5
<211> LENGTH: 46
<212> TYPE: DNA
<213> ORGANISM: Borrelia burgdorferi
<220> FEATURE:
<221> NAME/KEY: misc_feature
<222> LOCATION: (28)..(28)
<223> OTHER INFORMATION: "n" at position 28 represents OspC

<400> SEQUENCE: 5
ctggttccgc gtggatccaa taattcanaa aaaaccttag aattca                  46

<210> SEQ ID NO 6
<211> LENGTH: 13
<212> TYPE: PRT
<213> ORGANISM: Borrelia burgdorferi
<220> FEATURE:
<221> NAME/KEY: misc_feature
<222> LOCATION: (10)..(10)
<223> OTHER INFORMATION: "Xaa" at position 10 represents OspC

<400> SEQUENCE: 6

Leu Val Pro Arg Gly Ser Asn Asn Ser Xaa Lys Lys Pro
1               5                   10
```

MEDICAMENT FOR TREATING A MANIFESTED LYME DISEASE

DESCRIPTION

The invention concerns a pharmaceutical composition for treating Lyme disease and a vaccine against Lyme disease and it also concerns a process for obtaining an active agent for treating Lyme disease and a process for obtaining a vaccine against Lyme disease.

Lyme borreliosis is an infectious disease transmitted by ticks and is caused by the spirochete *Borrelia burgdorferi*. The disease is a chronic, progressive infection which attacks many organs, such as the skin, the central and peripheral nervous system, the heart, the liver, the kidneys, the musculoskeletal system and joints. Various symptoms such as acute arthritis and neuroborreliosis can disappear spontaneously but usually reoccur episodically. Spirochetes have been repeatedly isolated from untreated patients and there are numerous indications for persistent infections even after treatment with antibiotics. Since a dependable treatment of this disease by therapy with antibiotics is difficult, great efforts are being made to investigate the pathogen itself and the immune response of the host to infection with *B. burgdorferi*. Although a high titre of antibodies against *B. burgdorferi* is usually found during infection in persons afflicted by Lyme disease, this does not protect against the infection.

It was found that the outer surface lipoprotein A (OspA) of *B. burgdorferi* could be an effective vaccine for the prevention of Lyme disease (EP 0 418 827). Laboratory investigations on mice have shown that a substantial protection against the disease and infection can be obtained by OspA-specific antibodies (Schaible et al., Proc. Natl. Acad. Sci. USA 87 (1990), 3768–3772).

However, these antibodies are only effective if they are present when the pathogen is transmitted. A reason for this may be that OspA is mainly expressed on spirochetes in ticks but is no longer expressed after transmission to a mammalian host. Consequently it is indeed possible to use OspA-specific antibodies to prevent transmission of the disease but they are ineffective and thus unsuitable for therapeutic applications to treat the manifest disease. Recent investigations have shown that mice can be protected against a tick-transmitted infection after active immunization with recombinant OspC (Preac-Mursic et al., Infection 20 (1992), 342–349; R. D. Gilmore et al., Infect. Immun. 64 (1996), 2234–2239). However, the immunization protocol used in these investigations does not lead to an elimination of infectious spirochetes from the vector as was shown for the OspA-specific antibodies.

Hence the object of the invention was to provide a pharmaceutical preparation for treating Lyme disease.

This object is achieved according to the invention by a pharmaceutical composition for treating Lyme disease which is characterized in that it comprises an antibody as an active agent which is specific for the 24 kDa antigen (OspC) of *B. burgdorferi*. It was surprisingly found that high titres of OspC-specific antibodies resulted in a spontaneous disappearance of the disease and/or elimination of spirochetes in various species of mice. The pharmaceutical composition for treating Lyme disease preferably contains an antibody as the active agent which is specific for the 24 kDa antigen (OspC) of *B. burgdorferi* having the sequence shown in SEQ ID NO.2.

It surprisingly turned out that the passive transfer of polyclonal OspC-reactive immune serum into *B. burgdorferi*-infected scid mice leads to a complete disappearance of chronic arthritis and carditis and to elimination of the pathogen. A critical threshold of OspC-specific antibodies which is between 3 and 10 µg anti-OspC antibody appears to be important to effectively treat an infection. This means that spirochetes express OspC in the mammalian host and are sensitive to protective antibodies in the affected tissue during infection. Thus an attack on OspC is relevant for a successful therapeutic treatment of Lyme disease.

Earlier investigations have shown that immune sera from *B. burgdorferi*-infected mice only ensure a complete protection against disease and infection when they have been administered before but not after inoculation with the pathogen. In the present invention it is shown that antibodies against OspC can lead to a spontaneous disappearance of the infection and inactivation of the spirochetes in the vertebrate. Furthermore it was found that it is possible to eliminate arthritis and carditis with polyclonal OspC-specific immune sera and to heal existing spirochete infections in C.B.-17 scid mice irrespective of whether the antibodies were administered before the disease occurred (e.g. 10 days before infection) or alternatively at a time when the disease had completely broken out (on day 19 after infection) or whether it was a chronic disease (day 60 after infection). The complete disappearance of the disease and elimination of the pathogen were dose-dependent and were achieved with 1 µg to 10 mg anti OspC antibody/mouse, preferably 5 µg to 20 µg anti OspC antibody/mouse.

Inflammatory lesions of the joints or in the heart of *B. burgdorferi*-inoculated scid mice were completely eliminated by polyclonal immune sera against OspC even when they were administered at a time when a chronic disease was present i.e. on the 60th day p.i.

In the following the invention is illustrated by the figures of the drawing and the examples.

Figure legends:

FIG. 1 shows a Western blot analysis of NMS and IS which were used to passively immunize C.B.-17 scid mice. Lane 1 shows a standard of mouse mABs against Hsp70 (70 kDa), Hsp60 (60 kDa), flagellin (41 kDa), OspB (34 kDa), OspA (31 kDa), OspC (24 kDa), pLA7 (20 kDa) and p7.5 (7.5 kDa). Lane 2: NMS collected from naive BALB/c mice. Lane 3: polyclonal immune serum formed in BALB/c mice, immunized with rLip-OspA in ABM2 adjuvant. Lane 4: polyclonal IS formed in BALB/c mice, immunized with rOspC in ABM2 adjuvant as described herein.

FIG. 2

Kinetics of the occurrence of *B. burgdorferi*-specific (IgG) of OspC-specific (IgM/IgG) antibodies (A) and correlation analysis of serum contents of either total *B. burgdorferi*-specific or OspC-specific antibodies (IgG) and elimination of spirochetes from infected mice (B). AKR/N, C57BL/6 and BALB/c mice (6 to 8 weeks old) were infected by needle injection of $10^3$ spirochetes into the tail (s.c.). The amounts of *B. burgdorferi*-specific (IgG) and OspC-specific antibodies (IgM and IgG) in sera of individual mice were examined with an ELISA using either total cell lysates (*B. burgdorferi* strain ZS7) or rOspC (ZS7) as substrates. The data represent the mean of individual examined serum samples (AKR/N and C57BL/c: 10 mice/group; BALB/c: 7 mice; A). The correlation between the serum contents of total *B. burgdorferi*-specific IgG antibodies, OspC-specific IgG antibodies (day 23 p.i.) and the possibility of reculturing (day 90 p.i.) spirochetes from ear tissue was analysed by a correlation assay (B).

TABLE 1

Different therapeutic effects of immune sera against OspA and OspC on established
B. burgdorferi infections of C.B.-17 scid mice

| time intervals of the serum transfer (days p.i.) | transferred serum (dose) | mouse No. | Clinical arthritis (days p.i.) | | | | | | | ear tissue culture (days p.i.) |
|---|---|---|---|---|---|---|---|---|---|---|
| | | | 10 | 19 | 30 | 40 | 50 | 70 | 80 | 40 |
| −1 h | NMS 100 μl/mouse | 1 | −/± | ±/± | ++/+ | ++/++ | | | | + |
| | | 2 | (±)/− | ±/++ | + | ++/++ | ++/++ | ++/++ | ++/++ | + |
| | | 3 | −/− | ±/± | ++/+ | ++/++ | ++/++ | ++/++ | ++/++ | + |
| | | 4 | −/± | ++/+ | + | ++/++ | ++/++ | ++/++ | ++/++ | + |
| | | 5 | −/− | ++/+ | ++/+ + ++/+ + ++/+ + | ++/++ | ++/++ | ++/++ | ++/++ | + |
| | anti-OspA I.S. (3 μg/mouse) | 1 | −/− | ±/− | (±)/− | (±)/− | (±)/− | ±/− | ±/− | − |
| | | 2 | −/− | −/− | −/− | −/− | | | | − |
| | | 3 | −/− | −/− | −/− | −/− | −/− | −/− | −/− | − |
| | | 4 | −/− | −/− | −/− | −/− | −/− | −/− | −/− | − |
| | | 5 | −/− | −/− | −/− | −/− | −/− | −/− | −/− | − |
| | anti-OspC I.S. (3 μg/mouse) | 1 | −/− | −/− | −/− | −/− | | | | − |
| | | 2 | −/− | −/− | −/− | −/− | −/− | −/− | −/− | − |
| | | 3 | −/− | −/− | −/− | −/− | −/− | −/− | −/− | − |
| | | 4 | −/− | −/− | −/− | −/− | −/− | −/− | −/− | − |
| | | 5 | −/− | −/− | −/− | −/− | −/− | −/− | −/− | − |
| 10, 14 19, 22 | NMS 100 μl/mouse | 1 | −/− | +/++ | ++/+ | ++/++ | | | | + |
| | | 2 | −/− | (±)/− | + | ++/++ | ++/++ | ++/++ | ++/++ | + |
| | | 3 | (±)/− | ±/+ | +/+ | ++/++ | ++/++ | ++/++ | ++/++ | + |
| | | 4 | (±)/(±) | ±/+ | ++/+ | ++/++ | ++/++ | ++/++ | ++/++ | + |
| | | 5 | −/(±) | +/+ | + +/++ +/++ | ++/++ | ++/++ | ++/++ | ++/++ | + |
| | anti-OspA I.S. 10 μg/mouse | 1 | −/(±) | ±/± | ++/+ | ++/++ | | | | + |
| | | 2 | −/− | +/± | + | ++/++ | ++/++ | ++/++ | ++/++ | + |
| | | 3 | −/(±) | +/++ | ++/+ | ++/++ | ++/++ | ++/++ | ++/++ | + |
| | | 4 | (±)/(±) | ±/± | ++/+ | ++/++ | ++/++ | ++/++ | ++/++ | + |
| | | 5 | −/− | ±/++ | + ++/+ + ++/+ + | ++/++ | ++/++ | ++/++ | ++/++ | + |
| | anti-OspC I.S. (10 μg/mouse) | 1 | (±)/± | −/− | (±)/− | (±)/− | ±/− | ±/− | ++/± | + |
| | | 2 | −/(±) | −/− | −/− | −/− | | | | − |
| | | 3 | −/(±) | −/− | −/− | −/− | −/− | −/− | −/− | − |
| | | 4 | −/− | −/− | −/− | −/− | −/− | −/− | −/− | − |
| | | 5 | −/− | −/− | −/− | −/− | −/− | −/− | −/− | − |
| 19, 22, 26, 30 | NMS 100 μl/mouse | 1 | −/− | −/− | ±/± | ±/± | ±/± | ±/± | ±/± | + |
| | | 2 | −/− | ±/± | ++/+ | ++/++ | | | | + |
| | | 3 | −/− | ±/+ | + | ++/++ | ++/++ | ++/++ | ++/++ | + |
| | | 4 | −/− | ++/+ | ++/+ | ++/++ | ++/++ | ++/++ | ++/++ | + |
| | | 5 | −/(±) | (±)/− | + ++/+ + −/− | −/− | −/− | −/− | −/− | − |
| | anti-OspA I.S. (10 μg/mouse) | 1 | −/− | ±/+ | ++/+ | ++/++ | | | | + |
| | | 2 | (±)/− | +/+ | + | ++/++ | ++/++ | ++/++ | ++/++ | + |
| | | 3 | −/− | ±/+ | ++/+ | ++/++ | ++/++ | ++/++ | ++/++ | + |
| | | 4 | −/− | −/− | + | −/− | −/− | −/− | −/− | − |
| | | 5 | −/(±) | ++/+ | ++/+ + −/− ++/+ + | ++/++ | ++/++ | ++/++ | ++/++ | + |
| | anti-OspC I.S. (10 μg/mouse) | 1 | −/− | ±/± | ±/(±) | (±)/− | | | | − |
| | | 2 | −/+ | ++/++ | ±/+ | ±/+ | −/± | −/± | −/± | − |
| | | 3 | −/− | ±/+ | ±/(±) | −/(±) | −/(±) | −/− | −/− | − |
| | | 4 | −/± | +/± | ±/(±) | ±/− | −/− | −/− | −/− | − |
| | | 5 | −/(±) | ++/++ | ±/+ | ±/+ | −/(±) | −/(±) | −/(±) | − |

TABLE 2

Therapeutic effect of an immune serum against OspC 60 days after infection of C.B.-17 scid mice with $10^3$ *B. burgdorferi* ZS7

| anti OspC serum (μg/mouse) | time interval of the serum transfer (days p.i.) | mouse | clinical arthritis (days p.i.) | | | | | | ear tissue culture of spirochetes | |
|---|---|---|---|---|---|---|---|---|---|---|
| | | | 10 | 19 | 60 | 70 | 80 | 100 | 1.(d38) | 2.(d80) |
| 0.3 | 10, 14 | 1 | −/− | +/++ | ++/++ | ++/++ | ++/++ | ++/++ | n.d. | + |
| | 19, 22 | 2 | −/− | ++/++ | ++/++ | ++/++ | ++/++ | ++/++ | n.d. | + |
| | | 3 | −/− | ++/++ | ++/++ | ++/++ | ++/++ | ++/++ | n.d. | + |
| 10 | | 1 | −/− | +/+ | ++/++ | ±/+ | −/± | −/± | + | − |
| | | 2 | −/− | ++/+ | ++/++ | ±/± | −/− | † | + | − |
| | | 3 | (±)/− | ++/++ | ++/++ | +/++ | (±)/(±) | −/(±) | + | − |

TABLE 3

Histopathological examination of affected organs from individual infected scid mice after a therapeutic treatment with immune sera

| time interval of the serum transfer (days p.i.) | transferred serum (dose) | necropsy day p.i. | clinical arthritis | histopathological examination | | | |
|---|---|---|---|---|---|---|---|
| | | | | joint | heart | liver | muscle |
| none | none | 10 | −/(±) | + | + | n.t.* | n.t. |
| | | 27 | ++/++ | ++ | ++ | ++ | + |
| −1 h | NMS 100 μl/mouse | 45 | ++/++ | +++ | ++ | − | + |
| | anti-OspA I.S. (3 μg/mouse) | 45 | −/− | + | − | − | − |
| | anti-OspC I.S. (3 μg/mouse) | 45 | −/− | − | − | − | − |
| 10, 14 19, 22 | NMS 100 μl/mouse | 45 | ++/++ | +++ | ++ | − | + |
| | anti OspA I.S. (10 μg/mouse) | 45 | ++/++ | +++ | + | − | ± |
| | anti OspC I.S. (10 μg/mouse) | 45 | −/− | − | − | − | − |
| 19, 22, 26, 30 | NMS 100 μl/mouse | 45 | ++/++ | +++ | +++ | ± | + |
| | anti OspA I.S. (10 μg/mouse) | 45 | ++/++ | +++ | +++ | ± | n.t.* |
| | anti OspC I.S. (10 μg/mouse) | 45 | ±/± | + | − | − | − | n.t.* not tested

EXAMPLE 1

Materials and Methods a) Mice and Infection with *B. burgdorferi*

Adult mice of the strains AKR/N (H-$2^k$), C57BL/6 (H-$2^b$), BALB/c (H-$2^d$) and C.B.-17 scid (H-$2^d$) were bred under specific pathogen-free conditions. Female animals between 6 and 8 weeks old were used for the experiments. The mice were inoculated subcutaneously (s.c.) in the tail with $1 \times 10^3$ low-passaged (two to four in vitro passages) *B. burgdorferi* organisms of the strains ZS7 (Schaible et al., Proc. Natl. Acad. Sci. USA 87 (1990), 3768–3772).

b) Recombinant Antigens

A complete recombinant lipid OspA (rLip-OspA) from *B. burgdorferi* strain ZS7 was prepared as described (Gern et al., Immunol. Lett. 39 (1994), 249–258). A glutathione-S-transferase OspC fusion protein (rOspC) from *B. burgdorferi* strain ZS7 was prepared using known methods (R. Wallich et al., Infect. Immun. 64 (1995), 3327–3353).

c) Polyclonal Immune Serum

Figure 1:
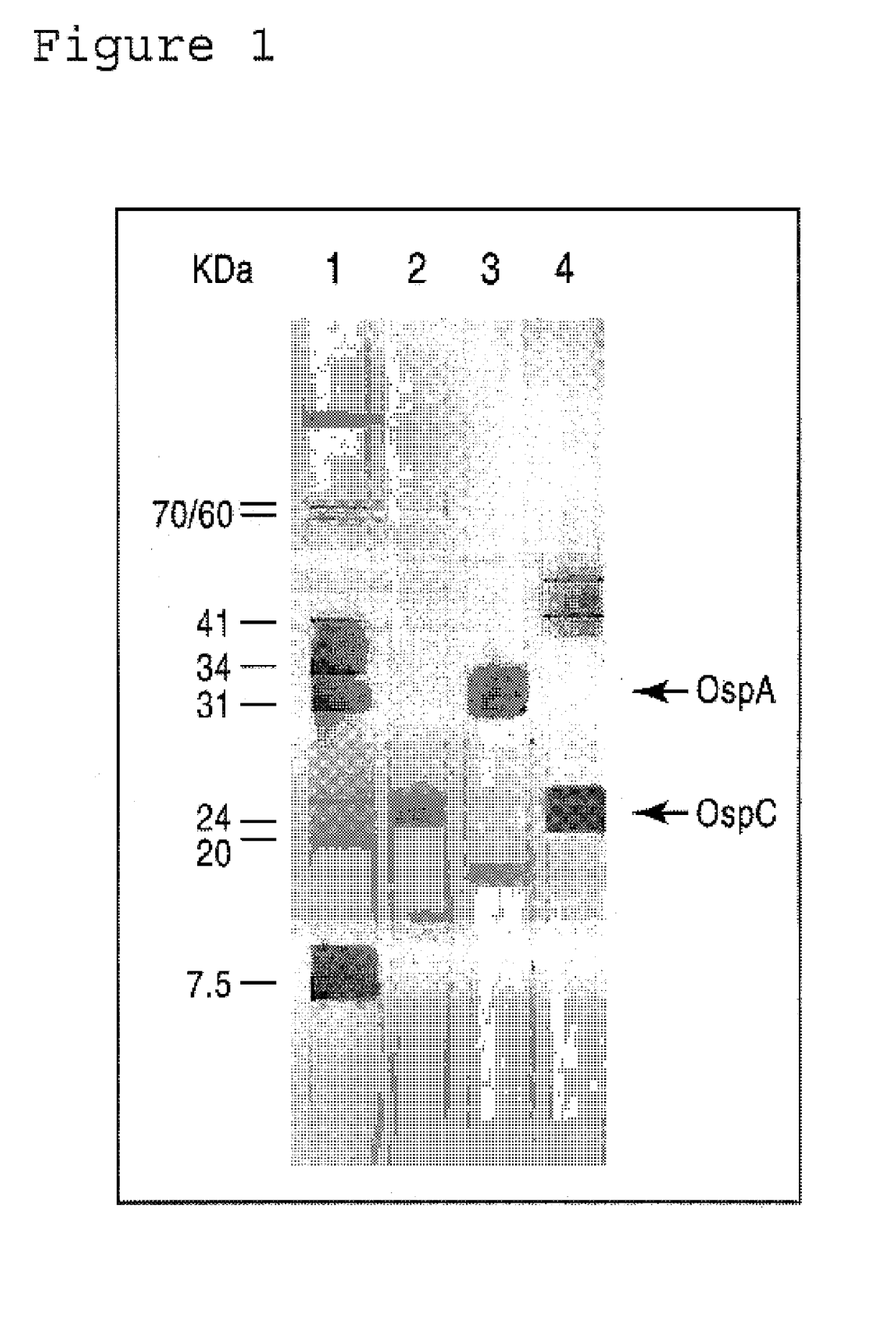

BALB/c mice were inoculated in the tail with either 10 μg rLip-OspA or 10 μg rOspC in 100 μl ABM2 adjuvant (Sebak, Aldenbach, Germany) and were boosted twice with the same antigen preparation at intervals of 10 days. The immune serum (IS) was collected over a period of about 2 months after the last boost and contained the following concentrations of OspA- or OspC-specific antibodies (Ab) as determined with an ELISA using rLip-OspA or rOspC as the substrate: anti-OspA IS, 3.2 mg/ml or anti-Ospc IS, 300 μg/ml. Normal mouse serum (NMS) was collected from naive BALB/c mice. The specificities of the produced immune sera and NMS were verified by Western blot analysis. As shown in FIG. 1 (lane 3, 4) a polyclonal immune serum from either OspA- or OspC-immunized mice reacted selectively with 31 kDa (OspA) or 24 kDa (OspC) proteins from a total cell lysate of ZS7 spirochetes. No reactivity with NMS was found (FIG. 1, lane 2).

d) Analysis of Serum Antibodies by ELISA and Western Blot

Serum antibodies against B. burgdorferi OspA or OspC were quantified by a solid phase ELISA as described in the prior art (Kramer et al., Immunobiol. 181 (1990), 357–366) using 1 µg/ml total cell lysate from B. burgdorferi strain ZS7, rLip-OspA (ZS7) or rOspC (ZS7) as substrates. The Western blot analysis was carried out using a total cell lysate of the B. burgdorferi strain ZS7 as the antigen preparation as described in the prior art (M. M. Simon et al., J. Infect. Dis. 164 (1991), 123–132).

e) Passive Transfer of Immune Serum to Protect Against and to Treat an Infection For the passive protection 6 to 8 week old female C.B.-17 scid mice were injected intraperitoneally (i.p.) either with an OspA- or an OspC-reactive polyclonal immune serum 1 hour before infection. Control mice received 100 µl NMS. The mice were infected by injecting $1\times10^3$ B. burgdorferi ZS7 organisms s.c. into the tail. Alternatively for the passive treatment of an existing infection scid mice were firstly infected with $1\times10^3$ ZS7 spirochetes (s.c.) and they were subsequently repeatedly (four times at intervals of 3 to 4 days) administered various amounts of polyclonal immune serum, which was either specific for OspA or OspC (i.p.) beginning on day 10, 19 or 60 after the infection (p.i.). The animals were observed with regard to the development of clinical arthritis in the tibiotarsal joints. The severity of the arthritis in the right and left tibiotarsal joint was assessed as follows: ++, severe; +, moderately severe; ±, mild swelling; (±), reddening; –, no clinical signs.

At the stated times the mice were examined for the presence of spirochetes by culturing ear tissue specimens using the procedure described in the prior art (Sinsky et al., J. Clin. Microbiol. 27 (1989), 1723–1727).

The mice were sacrificed at the stated times after infection for histopathological examinations. The tibiotarsal joint, the heart, the liver and the muscles adjoining the tibiotarsal joint were fixed in 10% formaldehyde, embedded in paraffin and stained with haematoxylin and eosin. The inflamed lesions were assessed as follows: +++, very severe; ++, severe, +, moderate; ±, mild; –, none.

EXAMPLE 2

Results

Figure 2:
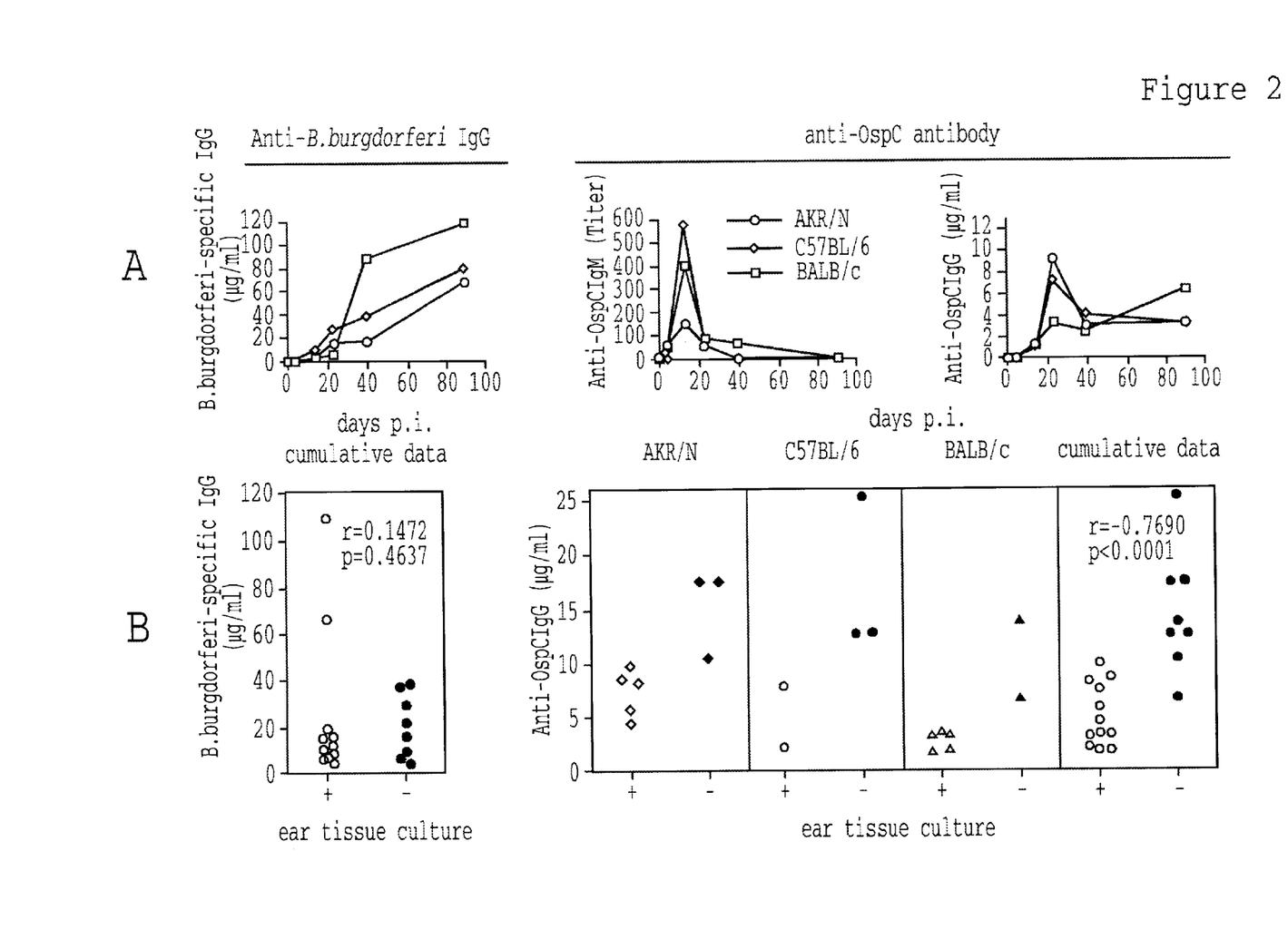
Figure 3:
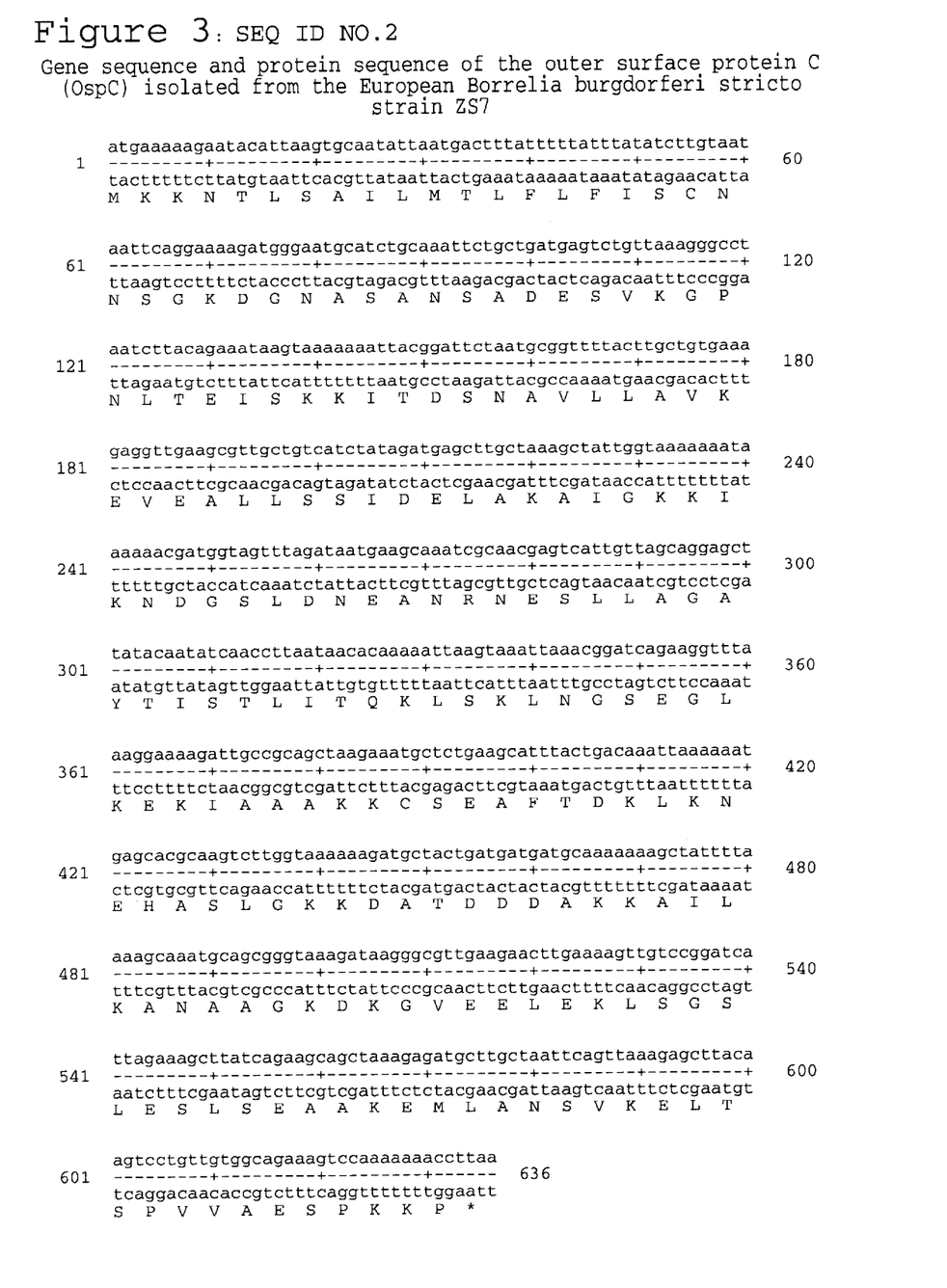
FIG. 3 shows the DNA (SEQ ID NO:1) sequence and the protein sequence of the 24 kDa antigen (OspC) of *B. burgdorferi* (SEQ ID NO. 2).
Figure 4:
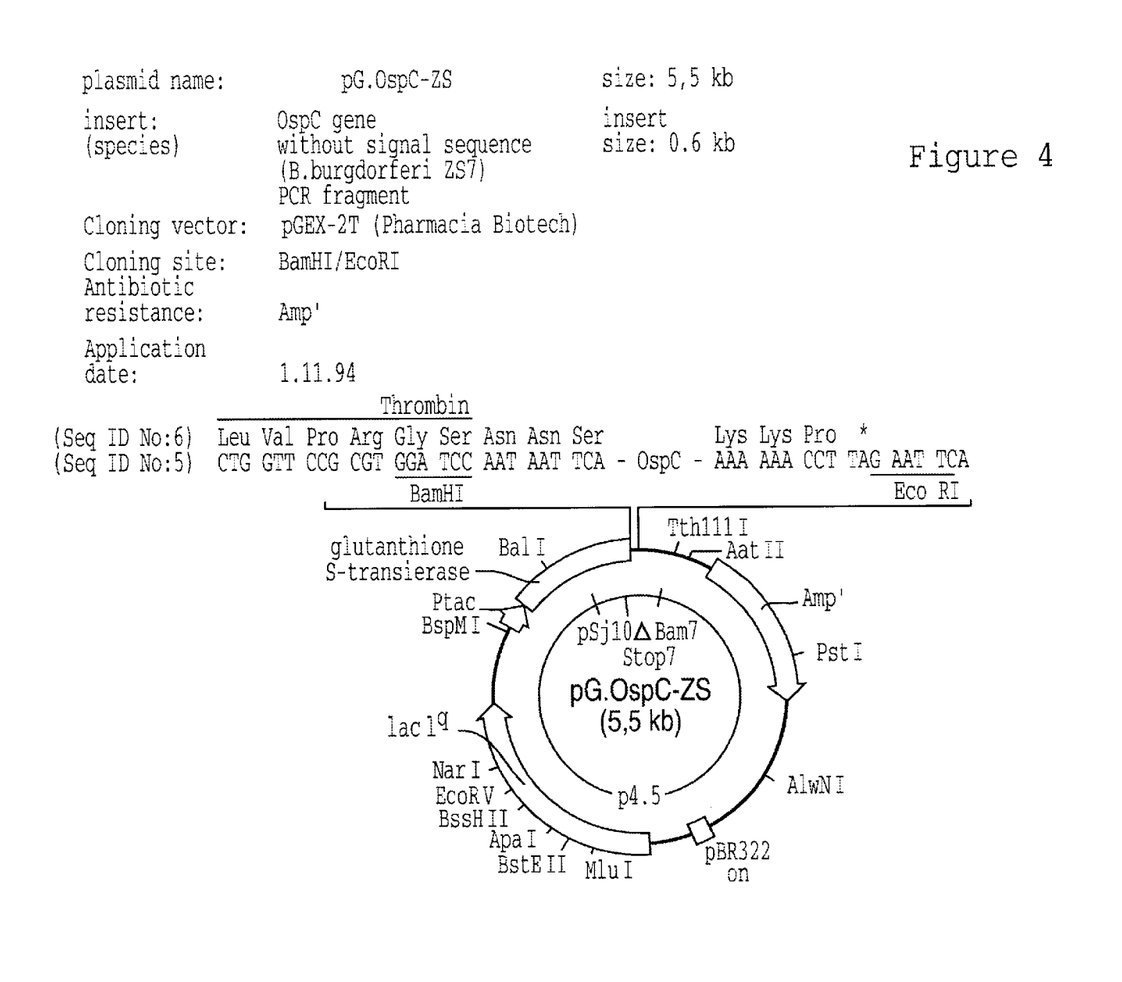
FIG. 4 shows the construction of the plasmid pG OspC-ZS which contains the OspC gene.

Three inbred mouse strains, AKR/N, BALB/c and C57BL/6 with different sensitivities towards a B. burgdorferi-induced disease (U. E. Schaible et al., Eur. J. Immunol. 21 (1991), 2397–2405) were infected with $10^3$ spirochetes. The kinetics of the specific antibody responses, development of arthritis and the persistence of spirochetes was observed for up to 90 days after infection. All animals inoculated with B. burgdorferi were infected as shown by seroconversion (FIG. 2A). All animals formed similar amounts of B. burgdorferi-specific IgG antibodies which were firstly detectable on the 14th day after infection and increased continuously during the entire observation period. In addition all mice developed considerable but variable amounts of OspC-specific IgM and IgG antibodies (FIG. 2A). OspC-specific IgM antibodies were only detectable on the 4th day after infection, reached a peak on the 14th day after infection and then decreased to baseline values on the 24th day after infection. OspC-specific IgG antibodies were initially observed on the 14th day after infection with a peak on the 23rd day after infection (peak values for AKR/N, C57BL/6: about 8 µg/ml; BALB/c: about 3 µg/ml). The antibody titre in AKR/N and C57BL/6 mice decreased with time but remained at detectable levels (about 3 µg/ml) up to 90 days p.i. In contrast BALB/c mice formed small amounts of OspC-specific IgG antibodies in the early phase of infection but the serum titre increased after infection. As expected from earlier studies (Schaible et al., Immunol. Lett. 36 (1993), 219–226; L. Gern et al., J. Infect. Dis. 167 (1993), 971–975) no antibodies against OspA were detectable in any of the sera of infected mice during the entire observation period of 90 days neither by ELISA nor by Western blot analysis using a spirochetal lysate or recombinant OspA.

A close correlation was found between the serum titres of anti-OspC antibodies and the spontaneous disappearance of the infection. As shown in FIG. 2B the amount of OspC-specific IgG antibodies in the 8 mice from which it was not possible to reculture any spirochetes was considerably higher than in those that were obtained from the positive cultures (10±5 µg/ml compared to 4.8±2.8 µg/ml). On the other hand no correlation was found between the total content of B. burgdorferi-specific IgG antibodies and the elimination of spirochetes. This shows that OspC-specific antibodies are able to inactivate spirochetes in vertebrates and to fight an infection.

EXAMPLE 3

Passive transfer experiments were carried out to examine whether polyclonal immune serum which is specific for rOspC can be used to heal a proven B. burgdorferi infection in scid mice. A polyclonal immune serum specific for rLip-OspA served as the control. It was found that different doses of OspC-specific antibodies were necessary for the prevention and treatment of the infection. A passive transfer of 3 µg OspC-specific antibodies into scid mice 1 hour before infection led to a complete protection against the disease and against infection in all examined mice (table 1). As previously shown a complete protection was also observed with 3 µg OspA-specific antibodies but not with normal mouse serum under similar conditions (table 1 and M. M. Simon et al., J. Infect. Dis. 164 (1991), 123–132). In contrast a repeated administration of 3 µg/mouse OspC-specific antibodies (4×at time intervals of 3 to 4 days) begun on the 10th day after infection, a time at which spirochetes have spread and the inflammation of joints and heart has started, only partially prevented the development of clinical arthritis. Spirochetes could not be inactivated in this amount.

Hence immune sera were used for the passive transfer experiments which contained 10 µg anti-OspC antibodies. As shown in table 1 such an immune serum administered repeatedly (10 µg, 4× at intervals of 3 to 4 days) beginning on day 10 or day 19 after the infection completely prevented the occurrence of and healed manifest clinical arthritis in all infected scid mice. Spirochetes could not be recultured from the ear tissue specimens. In contrast and as expected from earlier experiments (Schaible et al., Proc. Natl. Acad. Sci. USA 87 (1990), 3768–3772) a repeated passive transfer of similar amounts of anti-OspA-specific antibodies on the 10th or 19th day had no effect on clinical arthritis and infection. It is highly remarkable and surprising that anti-OspC-specific antibodies were able to eliminate a chronic disease and infection in mice. This is illustrated by the fact that the passive transfer of the respective immune serum starting on the 60th day after infection led to a considerable reduction of clinical arthritis within 10 days after treatment and to an almost complete disappearance during the following 30 days (table 2). Whereas the pathogen could be recultured from the ear tissue of all infected scid mice before treatment (on day 38 p.i.), none of the specimens which were taken from the same animals on the 20th day after the antibody transfer (day 80 p.i.) contained detectable amounts of spirochetes. No recurrence of clinical arthritis was observed up to 40 days after treatment irrespective of

EXAMPLE 4

The therapeutic effect of a polyclonal immune serum which is directed against OspC on an existing disease and infection of scid mice was additionally confirmed by histophathological examinations of the affected organs. As shown in table 3 significant histopathological changes were found in the joints, in the heart, in the liver and in the muscle of infected but otherwise untreated scid mice or in those that only received NMS. As shown previously (U. E. Schaible et al., Am. J. Pathol. 137 (1990), 811–820) chronic progressive inflammatory changes were usually found in tibiotarsal joints, in the heart and in the liver and remained during the entire observation period (45 days after infection). Mice which had received an immune serum either for OspC or OspA (3 μg specific antibody/mouse) 1 hour before infection exhibited no pathological changes in one of the four organs when examined on the 45th day after infection. Moreover mice which had received an immune serum directed against OspC (10 μg specific antibody/mouse) on the 10th or 19th day after the inoculation exhibited, if at all, only slight inflammatory lesions in the joints, heart, liver and muscle. In contrast immune serum directed against OspA (10 μg specific antibody/mouse) had no effect on the development or progression of the inflammation in the affected organs (day 19 after infection).

EXAMPLE 5

Preparation of OspC-GST Fusion Protein and Purification of Recombinant OspC

OspC was cloned into the expression vector pGEX-2T as follows:

1) amplification of the OspC gene from amino acid 20–211 by means of PCR
   (primers: ATGGATCCAATAATTCAGGAAAA-GATGGG and ATGAATTCCTAAGGTTTTTTTGGACTTTCTACC)
2) cloning the PCR fragment into pGEX-2T after BamHI/EcoRI digestion
3) transformation of E. coli DH5a
4) expression of rec. OspC-GST according to the manufacturer's instructions (Pharmacia Biotech)
5) purification of OspC-GST by glutathione seph. 4B columns
6) cleavage of OspC-GST by means of thrombin and purification. For this four OspC-GST protein preparations were digested overnight with thrombin protease and OspC were separated from GST by means of a glutathione seph. 4B column.

What is claimed is:

1. A pharmaceutical composition for treating Lyme disease, comprising an antibody as an active agent which is specific for the 24 kDa antigen (OspC) of *B. burgdorferi* having the sequence shown in SEQ ID NO. 2.

2. A pharmaceutical composition for treating Lyme disease, comprising at least one antibody as an active agent which is specific for the 24 kDa antigen (OspC) of *B. burgdorferi*.

3. The pharmaceutical composition according to claim 2, wherein said antibody is a polyclonal antibody which is specific for OspC.

4. The pharmaceutical composition according to claim 2, wherein said antibody binds to recombinant OspC from *P. burgdorferi* of the strain ZS7.

5. The pharmaceutical composition according to claim 2, wherein said antibody is of the IgG and/or IgM class.

6. The pharmaceutical composition according to claim 2, further comprising carriers for intraperitoneal administration.

7. The pharmaceutical composition according to claim 2, wherein said antibody is present in an amount between 1 μg to 10 mg.

8. A method for preventing the progression of arthritis and carditis and promoting healing of arthritis and carditis in animals that have been infected with viable pathogenic *B. burgdorferi* organisms, comprising administering the pharmaceutical composition according to claim 2 to said animals.

9. The method according to claim 8, wherein said method prevents the progression of arthritis and carditis in immune-deficient scid mice that have been infected with viable pathogenic *B. burgdorferi* organisms of the strain ZS7.

10. The method according to claim 8, wherein said method leads to the inactivation of spirochetes in immune-deficient experimental animals that have been infected with viable pathogenic *B. burgdorferi* organisms.

11. A vaccine against Lyme disease, comprising at least one antibody as an active agent which is specific for the 24 kDa antigen (OspC) of *B. burgdorferi*.

12. The vaccine according to claim 11, wherein said antibody is specific for the 24 kDa antigen (OspC) of *B burgdorferi* having the sequence shown in SEQ ID NO. 2.

13. The vaccine according to claim 11, wherein said antibody is a polyconal antibody which is specific for OspC.

14. The vaccine according to claim 11, wherein said antibody is specific for recombinant OspC from *B. burgdorferi* of the strain ZS7.

15. The vaccine according to claim 11, wherein said antibody is of the IgG and/or IgM class.

16. The vaccine according to claim 11, said vaccine prevents the development of arthritis and carditis in immune-deficient experimental animals that have been infected with viable pathogenic *B. burgdorferi* organisms.

17. The vaccine according to claim 11, wherein said antibody is present in an amount between 0.1 μg to 1 mg.

18. The vaccine according to claim 11, further comprising antibodies which are specific for the 31 kDa antigen (OspA) of *B. burgdorferi*.

* * * * *